United States Patent [19]

Hector

[11] Patent Number: 5,030,619

[45] Date of Patent: Jul. 9, 1991

[54] SYNERGISTIC FUNGICIDAL COMPOSITION

[75] Inventor: Richard F. Hector, Dublin, Calif.

[73] Assignee: Miles Inc., Elkhart, Ind.

[21] Appl. No.: 509,433

[22] Filed: Apr. 16, 1990

[51] Int. Cl.$^5$ ............................................. A61K 31/71
[52] U.S. Cl. ............................................. 514/8; 530/317; 514/383; 514/50; 514/23
[58] Field of Search ................... 530/317; 514/383, 50, 514/43, 23

[56] References Cited

U.S. PATENT DOCUMENTS

| | | | |
|---|---|---|---|
| 4,287,186 | 9/1981 | Zahner et al. | 514/50 |
| 4,293,489 | 10/1981 | Debono | 530/317 |
| 4,315,922 | 2/1982 | Hagenmaier et al. | 514/43 |
| 4,755,521 | 7/1988 | Kramer et al. | 514/383 |
| 4,851,389 | 7/1989 | Hector | 514/23 |
| 4,914,087 | 4/1990 | Hector et al. | 514/50 |
| 4,931,352 | 6/1990 | Fromtling et al. | 530/317 |

Primary Examiner—Lester L. Lee
Assistant Examiner—S. G. Marshall
Attorney, Agent, or Firm—James A. Giblin

[57] ABSTRACT

A fungicidal composition comprising a nikkomycin and an echinocandin B. Method of treating a fungal infection comprising administering therapeutically effective amounts of a combination of the nikkomycin and the echinocandin B. Composition and method are especially useful in treating infections of filamentous fungi. Combination of nikkomycin Z and cilofungin found to be synergistic against aspergillosis.

15 Claims, 2 Drawing Sheets

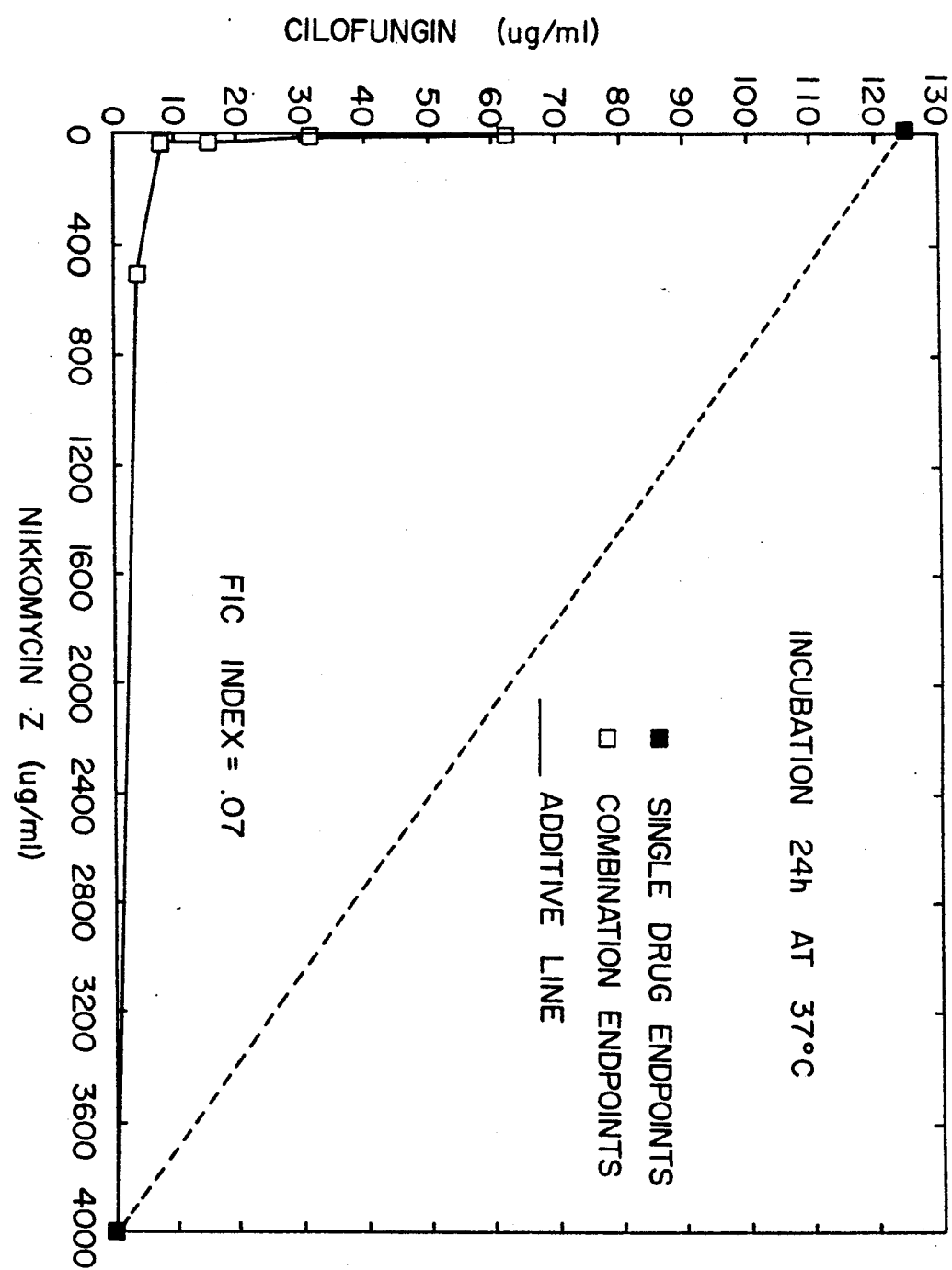

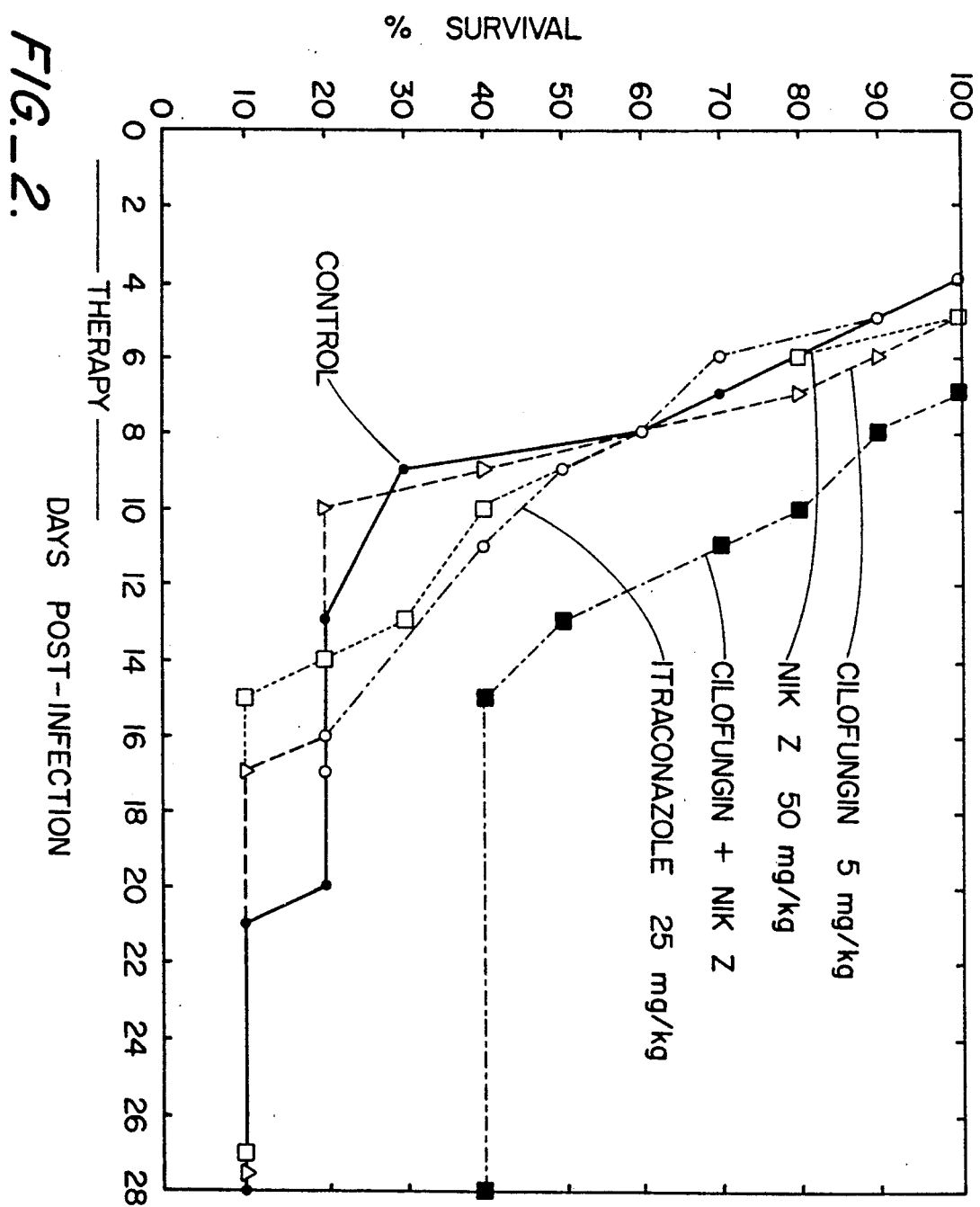
FIG._2.

SYNERGISTIC FUNGICIDAL COMPOSITION

FIELD

The invention is related generally to antimycotic compositions and specifically to compositions comprising fungicidally effective amounts of a nikkomycin and an echinocandin B.

PRIOR ART

Compounds inhibitory to the synthesis of fungal cell wall material (synthase inhibitors) have been reported recently to have demonstrable effects against fungi of agricultural importance (See U.S. Pat. Nos. 4,315,922 and 4,158,608; see also U.S. Pat. Nos. 4,585,761 and 4,552,954 for descriptions of the preparation and purification of such compounds), as well as against fungi of medical importance (See U.S. Pat. Nos. 4,851,389 and 4,288,548). The agents mentioned in the cited patents include nikkomycins, known to act by interfering with the synthesis of chitin in the cell wall of fungi. Another such agent was an echinocandin B known as cilofungin, which acts by interfering with the synthesis of beta-glucan in the cell wall.

Fungi of medical importance are known to have varying concentrations of chitin and beta-glucan in their cell walls (see, for example, Davis et al, Infect. Immun. 15:978–987, 1977). Experiments utilizing the aforementioned inhibitors singly, however, have shown each to be capable of inhibiting the growth of only a narrow spectrum of fungi. Indeed, in the case of cilofungin, the spectrum of activity appears limited to the medically important yeast, Candida (see Gordee, R.S., et al, J. Antibiotics 37:1054–1065, 1984 and M. Debono et al, Anm. N.Y. Acad. Sci. 544:152–167, 1988). Nikkomycins, on the other hand, are most effective against the parasitic growth phases of dimorphic, highly chitinous fungi such as *Coccidioides immitis* (see Hector, R. F., et al, Antimicrob. Agents Chemother. vol 34, No. 4, 1990).

The chemical structures of the nikkomycins are shown in the above-cited patents. The structures of echinocandin B compounds, including cilofungin (or LY121019) are shown in the above-cited M. Debono et al and R. S. Gordee et al publications.

Recently issued U.S. Pat. No. 4,914,087 to R. F. Hector et al discloses the use of certain nikkomycin derivatives in combination with an azole, resulting in synergistic fungicidal results.

Quite surprisingly, I have found that nikkomycin compounds in combination with an echinocandin B are efficacious and synergistic in treating infections due to filamentous fungi.

SUMMARY OF INVENTION

Combinations of a nikkomycin and an echinocandin B compound have been found effective in treating a mammal having an infection caused by filamentous fungi, especially an infection of Aspergillus. In one embodiment the nikkomycin is nikkomycin Z, administered with an echinocandin B known as cilofungin, in therapeutic amounts sufficient to treat infection of the filamentous fungus Aspergillus in a mammal (such as the mouse). The amounts of nikkomycin and cilofungin are enough to inhibit the enzymes chitin synthase and beta-glucan synthase, respectively. It is thought that the combined use of a chitin synthase inhibitor and a beta glucan synthase inhibitor will be especially useful in treating aspergillosis, especially aspergillosis caused by *A. fumigatus* infections. The nikkomycins or nikkomycin derivatives may be administered orally, topically, or parenterally and the cilofungin is administered parenterally or topically.

As shown in studies below, the achieved antifungal effect is a synergistic effect based on combining the nikkomycin with the cilofungin, and that this effect can be demonstrated in vivo in a mouse model of pulmonary aspergillosis.

BRIEF DESCRIPTION OF THE FIGURES

FIG. 1 is a graph showing synergistic results obtained using both Nikkomycin Z and cilofungin in vitro.

FIG. 2 is a graph comparing therapeutic results obtained using the indicated compounds alone and a combination of nikkomycin Z and cilofungin to treat pulmonary aspergillosis in a mouse model.

SPECIFIC EMBODIMENTS

Definitions

Therapeutically effective amount means an amount (commonly expressed as mg/kg body weight) of an antifungal compound or composition sufficient to result in clinical improvement in the signs and symptoms of disease and/or prevention of mortality in the more critically ill mammal infected with a fungus.

Pharmaceutically acceptable vehicle means a carrier suitable for delivering safe and efficacious amounts of a chitin synthase inhibitor such as a nikkomycin and a beta glucan synthase inhibitor such as an echinocandin B.

Materials and Methods

Strains and conditions of culture. *Asoergillus fumigatus* strain 13073 was employed in illustrative studies. For growth of conidia, plates of glucose yeast-extract agar were inoculated with a conidial suspension and allowed to grow at 37° C. for 7–10 days. The conidia were then harvested and stored in water at 4° C. until needed.

In Vitro Studies:

Susceptibility testing was performed in 96-well microtiter plates using yeast nitrogen broth with glucose and asparagine as the growth medium. Nikkomycin Z was dissolved directly in the growth medium while cilofungin was first dissolved in 95% ethanol and subsequently diluted in growth medium. The test materials were diluted serially, then transferred to the appropriate wells of the microtiter plates so that the final concentrations ranged from 3.9 to 4000 micrograms per milliliter for the nikkomycins and 1.9 to 125 micrograms per milliliter for the cilofungin.

All wells were inoculated with 10,000 conidia per milliliter (final concentration) and the plates incubated at 37° C. for 24 hours. The plates were examined microscopically, and the endpoints determined for each row as being the lowest concentration showing the complete inhibition of conidia germination. Data were plotted as isobolograms showing the endpoints for the various combinations.

In Vivo Studies:

Male DBA/2N mice, 21-23 grams average weight, were given a single injection of 5 mg of cortisone acetate subcutaneously 18 hours prior to infection. On the day of infection, mice were first anesthetized with pentobarbital (50 mg/kg given intraperitoneally), then 30 $\mu$l of inoculum containing $3 \times 10^4$ conidia of *A. fumiga-*

*tus* was placed on the nares of each mouse, which was then inhaled.

Six hours after infection, therapy was begun in groups of 10 mice each. Nikkomycin Z-treated mice received 50 mg/kg of the compound dissolved in dilute agar via the oral route, given twice daily. Cilofungin-treated mice received 5 mg/kg of the compound dissolved in 33% PEG 200/66% water delivered intraperitoneally twice daily. As a positive control, another group of mice was treated orally once daily with 25 mg/kg of itraconazole, an azole antifungal known to be effective. Animals were treated for 10 days, then held for an additional 20 days for observation.

Results

In vitro studies:

Examination of cultures at 24 hours revealed that neither drug singly was able to inhibit the germination and subsequent growth of the fungus at the highest concentration tested. Surprisingly, however, combinations of the two agents were able to inhibit germination at concentrations dramatically lower than the maximum single drug concentrations employed. See FIG. 1. Indeed, the calculated FIC index (see H. O. Hallander et al, Antimicrob. Agents Chemother. 22:743–752, 1982), which is a mathematical expression of the degree of synergy (with synergy defined as a value less than 0.5) is ≦0.07, indicating a profound synergistic effect.

Microscopically, most conidia treated with combinations of nikkomycin Z and cilofungin were swollen to several times their normal diameter, with many cells having burst, suggesting that inhibition of chitin and beta-glucan had led to an osmotically sensitive state.

In vivo studies:

Results with this severe infection model indicate that treatment with the single drugs nikkomycin Z, cilofungin, and itraconazole did not delay deaths in these groups in comparison to the control group (FIG. 2). Treatment with the combination of nikkomycin Z and cilofungin did delay rate of deaths and resulted in the protection of 40% of the animals. Although not shown, these animals were held for a total of 45 days, and no additional deaths occurred, suggesting that survivors had cleared the infection.

SUMMARY

The results of the in vitro assay demonstrated that while a nikkomycin (nikkomycin Z) and a echinocandin B (cilofungin) used singly had no effect on Asoeroillus. unexpectedly, the combination of these two agents had a marked inhibitory activity. The results of the in vivo model were confirmatory of these findings in that while the single drugs administered in a severe model of pulmonary aspergillosis were unable to prevent the rate of deaths in comparison to controls, simultaneous administration of the nikkomycin and the echinocandin B was able to both slow the rate of deaths and result in the survival of 40% of the animals.

Although the prior art teaches that combinations of chitin and beta-glucan synthase inhibitors used in combination are effective versus yeasts like *Candida albicans* (R. F. Hector and P. C. Braun, Antimicrob. Agents Chemother. 29: 389–394, 986), earlier work indicated that these combinations are not synergistic against the dimorphic, highly chitinous fungus *Coccidioides immitis*. Indeed, the complete absence of activity of nikkomycin Z or cilofungin when used singly against *Asoergillus fumigatus* would likely lead one skilled in the art to conclude that classes of fungi, i.e., yeasts, dimorphic fungi, filamentous fungi, etc., react differently and unpredictably with these agents. Indeed, the prior art with chitin synthase inhibitors singly demonstrated that even within the single dimorphic fungal species *Coccidioides immitis* the parasitic phase was very sensitive while the filamentous phase was resistant (R. F. Hector and D. Pappagianis, J. Bacteriol. 154:488–498, 1983), further demonstrating the unpredictable pattern of susceptibility of medically important fungi to inhibitors of cell wall synthesis.

Given the above disclosure, it is thought variations (such as ideal ratios of dosages, vehicles, etc.) will occur to those skilled in the art. For example, it is thought that the combinations of chitin synthase inhibitors and nikkomycins other than nikkomycin Z and and beta glucan synthase inhibitors echinocandin B compounds other than cilofungin may also be effective against infections in mammals by filamentous fungi other than Aspergillus.

Accordingly, it is intended that the above examples should be limited only the the following claims.

We claim:

1. An antimycotic composition comprising therapeutically effective amounts of a nikkomycin and an echinocandin B.

2. The composition of claim 1 wherein the echinocandin B is cilofungin.

3. The composition of claim 1 wherein the nikkomycin is selected from nikkomycin X and nikkomycin Z.

4. The composition of claim 1 wherein the nikkomycin nikkomycin Z and the echinocandin B is cilofungin.

5. A method of treating a mammal infected with a filamentous fungus, the method comprising administering to the mammal therapeutically effective amounts of a chitin synthase inhibitor and a beta glucan synthase inhibitor.

6. The method of claim 5 wherein the chitin synthase inhibitor is a nikkomycin and the beta glucan synthase inhibitor is an echinocandin B.

7. The method of claim 5 wherein the nikkomycin is nikkomycin Z or nikkomycin X and the echinocandin B is cilofungin.

8. The method of claim 7 wherein the fungus is *Aspergillus sp*.

9. The method of claim 8 wherein the fungus is *Aspergillus fumigatus*.

10. The method of claim 5 wherein the fungi have cell walls comprised of at least 10% by weight chitin and 10% by weight beta-glucan.

11. The method of claim 5 wherein the nikkomycin and the echinocandin B are administered in a pharmaceutically acceptable vehicle.

12. The method of claim 7 wherein the nikkomycin is administered either orally or parenterally and the cilofungin is administered parenterally.

13. The method of claim 7 wherein the nikkomycin and cilofungin are administered topically.

14. The method of claim 7 wherein the nikkomycin and the cilofungin are administered simultaneously.

15. The method of claim 14 wherein the nikkomycin is nikkomycin Z and it and the cilofungin are administered topically.

* * * * *